United States Patent [19]

Esper et al.

[11] Patent Number: 4,535,487
[45] Date of Patent: Aug. 20, 1985

[54] ENDOPROSTHESIS SHAFT

[75] Inventors: Friedrich J. Esper, Leonberg; Walter Gohl, Aidlingen, both of Fed. Rep. of Germany

[73] Assignee: Robert Bosch GmbH, Stuttgart, Fed. Rep. of Germany

[21] Appl. No.: 570,663

[22] Filed: Jan. 13, 1984

[30] Foreign Application Priority Data

Jan. 18, 1983 [DE] Fed. Rep. of Germany ....... 3301415

[51] Int. Cl.³ ............................................... A61F 1/00
[52] U.S. Cl. ................................... 623/22; 128/92 C; 128/92 CA; 623/18
[58] Field of Search ........................ 3/1.9, 1.91, 1.912, 3/1.913; 128/92 C, 92 CA

[56] References Cited

U.S. PATENT DOCUMENTS 4,068,324 1/1978 Townley et al. ..................... 3/1.913
4,356,571 11/1982 Esper et al. ................................. 3/1

FOREIGN PATENT DOCUMENTS 0011663 6/1980 European Pat. Off. ............. 3/1.913
2733826 2/1979 Fed. Rep. of Germany ......... 3/1.91
541963 11/1973 Switzerland ............................ 3/1.91

Primary Examiner—Richard J. Apley
Assistant Examiner—David J. Isabella
Attorney, Agent, or Firm—Frishauf, Holtz, Goodman & Woodward

[57] ABSTRACT

The load P on an artificial hip joint produces a bending moment on the endoprosthesis shaft composed of a shaft proper (1), a collar (2) fitting the resection plane and a cone (3) for carrying the femur ball (14). The extra load B thereby provided on the medial side of the femur is relieved by providing means for resisting the tension force A of the bending moment by providing the shaft with cavities (11) separated by ribs (12) as well as by a median longitudinal rib (broken lines). The bone grows into the cavities thus securing the area against the tension effects. Additional cavities (9) and wedge-shaped nubs (7) and (5) similarly oppose forces A and/or B. Hollows (10) on the underside of the collar (2), as well as the cavities (11) and (9), also oppose twisting forces.

12 Claims, 4 Drawing Figures

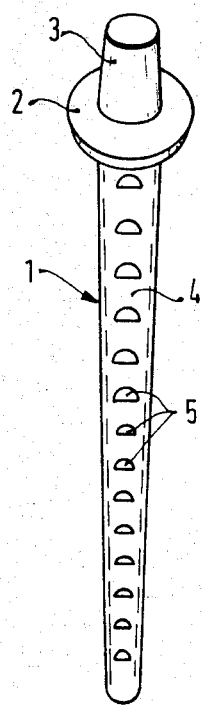
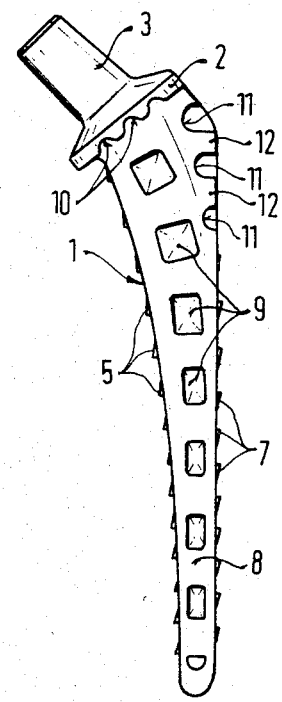
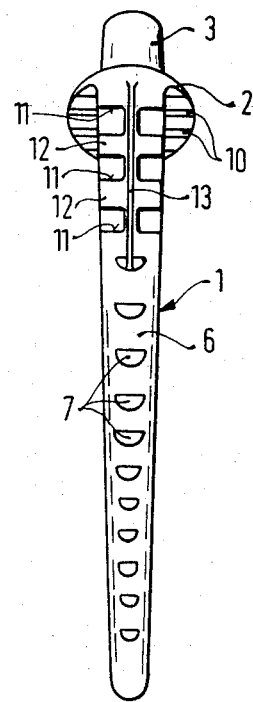
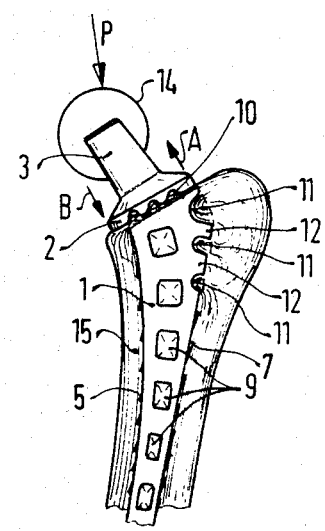

ENDOPROSTHESIS SHAFT

The invention concerns hip-joint endoprostheses and more particularly the tapered shaft which fits into a bore made in the upper part of the femur after it is resectioned and has a characteristic shape at its upper end, bending over a little towards an oblique collar fitting the resection and carrying a post on which the artificial femur ball is seated.

The femur component of a hip-joint endoprosthesis must be permanently and firmly anchored in the truncated end of the natural bone. To obtain that result, it is necessary to observe the Wolff transformation law, as described in J. Wolff, Das Gesetz der Transformation der Knochen, Hirschwald, Berlin, 1982. According to that principle, it is possible for the living remainder of the prosthetically equipped bone to accommodate to the play of forces necessarily disturbed by the resection only when that play of forces does not deviate too strongly from the natural course of such forces. Above all, it is important to avoid unphysiological concentrations of tension stress in the region of the resection plane. This means that the prosthesis shaft must be so constituted that the transfer of forces into the remaining thigh bone takes place evenly over the entire bone/prosthesis connection.

A shaft prosthesis with tension relief has already been proposed (compare A. Grünert, C. H. Schweickert, "Die Zuggurt-Hüftendoprotheses", Ber. orthop. Unfall-Chir. 86, 49–66, 1977). In this prosthesis, a tension flange is additionally provided between the lateral and medial sides of the prosthesis, which makes it necessary for both the remaining bone and also the prosthesis must be bored through for fastening the flange in order to be able to fasten the anchoring screw for the flange. Such a tension release is naturally complicated, requires a change of the operation technique—it becomes more difficult—and finally also requires new instrumentation compared to the prostheses not equipped with such tension relief.

SUMMARY OF THE INVENTION

It is an object of the present invention to provide an endoprosthesis shaft for the hip joint which will not require a substantial change in the hip-joint operation procedure and will in an uncomplicated way improve the junction of the prosthesis with the live bone against unbalanced tension and compression forces when the hip joint is loaded in normal use.

Briefly, the endoprosthesis shaft is provided with cavities or pits on the upper side, the so-called lateral side, which is to say the convexly bent side, of the upper end of the shaft. These leave ribs between them so that after the intrusion of bone tissue the shaft is fortified against displacement. In the preferred form of the shaft, these cavities are interrupted not only in a direction perpendicular to the length of the shaft, but also along the middle of the upper (convex) side of the shaft by a kind of web-like ridge or partly buried septum. The endoprosthesis shaft according to the invention has the advantage that the profiling of the shaft according to the invention stiffens the system of shaft and remaining bone in such a way that the loading conditions of the bone come close to those of the healthy femur (principally on the medial side). In particular, the flux of force in and near the resection plane approximates the natural conditions, so that undesired bone deformation and resulting loosening of the prosthesis are prevented. The operation technique does not need to be changed and the shaft profiling works out not to put any difficulties into the performance of the operation.

The preferred form with the interruption of the cavities in a direction of right angles to the length of the shaft and the provision of a solid strip in the middle of the upper side of the shaft has the advantage of providing highly effective security against the twisting of the prosthesis shaft, as well as securing against undesired slip from tension on the upper side of the shaft.

BRIEF DESCRIPTION OF THE DRAWINGS

The invention is further described by way of illustrative example with reference to the annexed drawings, in which:

FIG. 1a is an elevation view of an endoprosthesis shaft according to the invention from the side referred to as the underside (for reasons evident from FIG. 1b) and otherwise referred to as the medial side;

FIG. 1b is an elevation view from the so-called front or back side of the prosthesis shaft of FIG. 1a;

FIG. 1c is an elevation view from the upper side, the so-called lateral side of the prosthesis shaft of FIG. 1a, and FIG. 2 is a side view similar to FIG. 1b of the same prosthesis shaft showing it inserted in the femur, the femur being shown in section forward of the median plane, and also the ball of the joint, as well as a diagrammatic showing of forces acting on the shaft in response to a load P on the joint.

DESCRIPTION OF THE ILLUSTRATED EMBODIMENT

The endoprosthesis shaft illustrated in FIGS. 1a, 1b and 1c consist of the shaft proper 1, the collar 2, which as shown in FIG. 2 lies on the resection plane when the shaft is inserted in the bone, and a cone 3, actually a cone frustum, which serves as the carrier for the femur ball (not shown in FIGS. 1a, 1b and 1c) of the endoprosthesis. Nubs 5 for taking up or resisting compression force are located on the underside 4 of the shaft 1, whereas nubs 7 for taking up or resisting tension force are provided on the upperside 6 of the shaft 1. The surfaces 8 of the front or back side of the shaft are provided with cavities 9, providing the load-bearing effect of ribbing operative in the longitudinal direction of the shaft, which likewise have a relieving effect, especially for the medial femur region. The same holds for the hollows 10 on the underside of the shaft collar 2.

On the upper part of the so-called upper side 6 of the shaft 1, in the portion adjacent to the collar 2, there are cavities 11 with ribs 12 between them, the cavities 12 being interrupted in the middle of the upper side 6 with the formation of a continuous strip 13 that likewise is designed to oppose forces. What is postulated for taking up or resistance to forces in all cases above mentioned is that the bone grows as fast as possible, and without substantial formation of connecting tissue, into the cavities and against the ridges between them.

Shaft 1, collar 2 and cone 3 are of a single piece and can in principle be produced of any material suitable for such endoprostheses. Such a material which has been found particularly suitable is a composite material of triazine resin and carbon fibers, such as is described in German published patent application DE-OS 29 41 369 in connection with the manufacture of prostheses of such a material.

FIG. 2 shows the relative relation of forces in the prosthesis/bone junction. In this figure, the femur ball 14 is also shown. The remaining bone is designated 15. The applied load P produces a bending moment in the prosthesis shaft 1. In consequence, a supplementary load is produced in the bone region B. This load can be reduced by engagement with the tension forces in the region A. That occurs as the result of the tension relief ribs 12 on the upperside 6 of the shaft 1 when the bone, as already mentioned above, has grown into the cavities. The bone which has grown into the cavities 11 of the rib 12 picks up over a large area the tension forces on the lateral sides of the implant and thereby relieves the medial side, particularly the critical location at B.

Although the invention has been described with reference to a particular illustrative embodiment, it is evident that variations and modifications are possible within the inventive concept. For example, the cavities 9 might be reduced in number or omitted, and/or also the nubs 5 will still retain the benefit of the cavities 11 and the nubs 7.

We claim:

1. Endoprosthesis shaft for a hip joint having tension-release effect, said shaft having front, back, medial and lateral surfaces and being tapered for fitting into a bore in the top of a femur, said shaft having an oblique collar for fitting over the resected surface of the femur; and said lateral surface including tension force resisting means along a portion of the length thereof, said medial surface including compression force resisting means along the length thereof, said front and back surfaces including load-bearing means along the length thereof, said front and back surfaces further including a plurality of transversely formed, longitudinally spaced apart cavities located solely in the upper portion of said shaft adjacent said collar, each of said cavities being separated by transverse ribs, wherein said ribs and cavities are continuous about the juncture of said front, back and lateral surfaces and terminate in spaced apart relation on said lateral surface, said lateral surface having a continuous, longitudinally extending rib separating said ribs and cavities and terminating in the region of said tension resisting force means whereby said cavities accept tissue ingrowth thereby relieving tensional forces tending to shift said shaft relative to the bone.

2. Endoprosthesis shaft according to claim 1, wherein said cavities are interrupted in a direction perpendicular to the longitudinal direction of the shaft (1) by said ribs for separation of said cavities from each other and are also interrupted for further separation from each other by the formation of a ridge-like web in the middle of said upper side (6) of said shaft (1).

3. Endoprosthesis shaft according to claim 2, in which the extension of said upper side of said shaft extending into said bore is provided with nubs (5) shaped for opposing tension forces and the side of said shaft opposite said upper side and said extension thereof is equipped with nubs shaped for resisting compression forces.

4. Endoprosthesis shaft according to claim 3, in which the sides of said shaft on opposite sides of the plane of the curvature of the upper part of said shaft are provided with cavities (9) for resisting forces tending to displace said shaft in said bore.

5. Endoprosthesis shaft according to claim 2, in which the sides of said shaft on opposite sides of the plane of the curvature of the upper part of said shaft are provided with cavities (9) for resisting forces tending to displace said shaft in said bore.

6. Endoprosthesis shaft according to claim 1 in which the sides of said shaft on opposite sides of the plane of the curvature of the upper part of said shaft are provided with cavities (9) for resisting forces tending to displace said shaft in said bore.

7. Endoprosthesis shaft according to claim 1, in which said shaft consists of a composite material of triazine resin and carbon fibers.

8. Endoprosthesis shaft according to claim 2, in which said shaft consists of a composite material of triazine resin and carbon fibers.

9. Endoprosthesis shaft according to claim 3, in which said shaft consists of a composite material of triazine resin and carbon fibers.

10. Endoprosthesis shaft according to claim 4, in which said shaft consists of a composite material of triazine resin and carbon fibers.

11. Endoprosthesis shaft according to claim 5, in which said shaft consists of a composite material of triazine resin and carbon fibers.

12. Endoprosthesis shaft according to claim 6, in which said shaft consists of a composite material of triazine resin and carbon fibers.

* * * * *